US008790664B2

(12) United States Patent
Pitard et al.

(10) Patent No.: US 8,790,664 B2
(45) Date of Patent: Jul. 29, 2014

(54) MULTIMODULAR ASSEMBLY USEFUL FOR INTRACELLULAR DELIVERY

(75) Inventors: Bruno Pitard, Reze (FR); Charles Tellier, Notre Dame des Landes (FR); Corinne Miral, Treillieres (FR); Emilie Letrou-Bonneval, Limoges (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 593 days.

(21) Appl. No.: 13/062,339

(22) PCT Filed: Sep. 2, 2009

(86) PCT No.: PCT/IB2009/053830
§ 371 (c)(1),
(2), (4) Date: May 6, 2011

(87) PCT Pub. No.: WO2010/026537
PCT Pub. Date: Mar. 11, 2010

(65) Prior Publication Data
US 2012/0058139 A1  Mar. 8, 2012

(30) Foreign Application Priority Data
Sep. 5, 2008 (EP) .................................. 08305533

(51) Int. Cl.
*A61K 48/00* (2006.01)
(52) U.S. Cl.
CPC ................................. *A61K 48/0041* (2013.01)
USPC .................... 424/278.1; 424/280.1; 514/44 R
(58) Field of Classification Search
CPC ................................................... A61K 47/48
See application file for complete search history.

(56) References Cited

U.S. PATENT DOCUMENTS

| | | | |
|---|---|---|---|
| 6,353,055 B1 | 3/2002 | Kabanov et al. | |
| 6,884,430 B1 | 4/2005 | Crouzet et al. | |
| 7,470,781 B2 | 12/2008 | Crouzet et al. | |
| 7,709,452 B2 | 5/2010 | Pitard | |
| 2003/0018002 A1* | 1/2003 | Sagara | 514/44 |
| 2004/0132676 A1 | 7/2004 | Pitard | |
| 2005/0026287 A1 | 2/2005 | Crouzet et al. | |
| 2006/0134221 A1* | 6/2006 | Geall | 424/489 |
| 2010/0179212 A1 | 7/2010 | Pitard | |

FOREIGN PATENT DOCUMENTS

| | | |
|---|---|---|
| EP | 0 140 308 A2 | 5/1985 |
| EP | 0 185 573 A1 | 6/1986 |
| EP | 0 259 212 AI | 3/1988 |
| EP | 0 321 201 A2 | 6/1989 |
| EP | 394 111 A1 | 10/1990 |
| FR | 2 681 786 A1 | 4/1993 |
| FR | 2 688 514 A1 | 9/1993 |
| FR | 2 704 234 A1 | 10/1994 |
| WO | WO 96/17823 A1 | 6/1996 |
| WO | WO 97/18185 A1 | 5/1997 |
| WO | WO 03/018603 A1 | 3/2003 |
| WO | WO 2008/011431 A2 | 1/2008 |
| WO | WO 2008/040792 A2 | 4/2008 |

OTHER PUBLICATIONS

Martin et al., Advances in cationic lipid-mediated gene delivery; Gene Ther Mol Biol, vol. 7, 273-289, 2003.*
Behr, J. et al., "Efficient gene transfer into mammalian primary endocrine cells with lipopolyamine-coated DNA," *Proc. Natl. Acad. Sci. USA*, Sep. 1989, pp. 6982-6986, vol. 86.
Felgner, J. et al., "Enhanced Gene Delivery and Mechanism Studies with a Novel Series of Cationic Lipid Formulations," *The Journal of Biological Chemistry*, Jan. 24, 1994, pp. 2550-2561, vol. 269, No. 4.
Zanta, M. et al., "In Vitro Gene Delivery to Hepatocytes with Galactosylated Polyethylenimine," *Bioconjugate Chem.*, 1997, pp. 839-844, vol. 8.
Nishikawa, M. et al., Targeted Delivery of Plasmid DNA to Hepatocytes In Vivo: Optimization of the Pharmacokinetics of Plasmid DNA/Galactosylated Poly ($_L$Lysine) Complexes by Controlling their Physicochemical Properties, *The Journal of Pharmacology and Experimental Therapeutics*, 1998, pp. 408-415, vol. 287, No. 1.
Niidome, T. et al., "Gene transfer into hepatoma cells mediated by galactose-modified α-helical peptides," *Biomaterials*, 2000, pp. 1811-1819, vol. 21.
Remy, J. et al., "Targeted gene transfer into hepatoma cells with lipopolyamine-condensed DNA particles presenting galactose ligands: A stage toward artificial viruses," *Proc. Natl. Acad. Sci. USA*, Feb. 1995, pp. 1744-1748, vol. 92.
Baker, T. et al., "Synthesis and Anti-HIV Activity of Guanidinoglycosides," *J. Org. Chem.*, 2000, pp. 9054-9058, vol. 65.
Vigneron, J. et al., "Guanidinium-cholesterol cationic lipids: Efficient vectors for the transfection of eukaryotic cells," *Proc. Natl. Acad. Sci. USA*, Sep. 1996, pp. 9682-9686, vol. 93.
Stanton, W., "Block Polymer Surfactants," *American Perfumer and Cosmetics*, 1958, pp. 54, 56 and 58, vol. 72, No. 4.
Schmolka, I., "Application of Pluronic polyols in the cosmetic industry," *American Perfumer and Cosmetics*, Jul. 1967, pp. 25-30, vol. 82, No. 7.
Schick, M., "Nonionic Surfactants," *Solvent Properties of Surfactant Solutions*, 1967, pp. 300-371, vol. 2.

(Continued)

*Primary Examiner* — Celine Qian
*Assistant Examiner* — Addison D Ault
(74) *Attorney, Agent, or Firm* — Oliff PLC

(57) ABSTRACT

A stabilized multimodular assembly for intracellular delivery comprising a complex of at least one cationic transfection agent and of at least one negatively charged macromolecule, wherein the complex has a theoretical charge ratio ranging from about 0 to about 4, and an efficient amount of at least one amphiphilic block co-polymer acting as a steric colloidal stabilizer with respect to the complex, the block co-polymer having hydrophilic and hydrophobic blocks wherein at least one hydrophilic block is conjugated with at least one targeting ligand.

11 Claims, 5 Drawing Sheets

(56) References Cited

OTHER PUBLICATIONS

Figure 1:
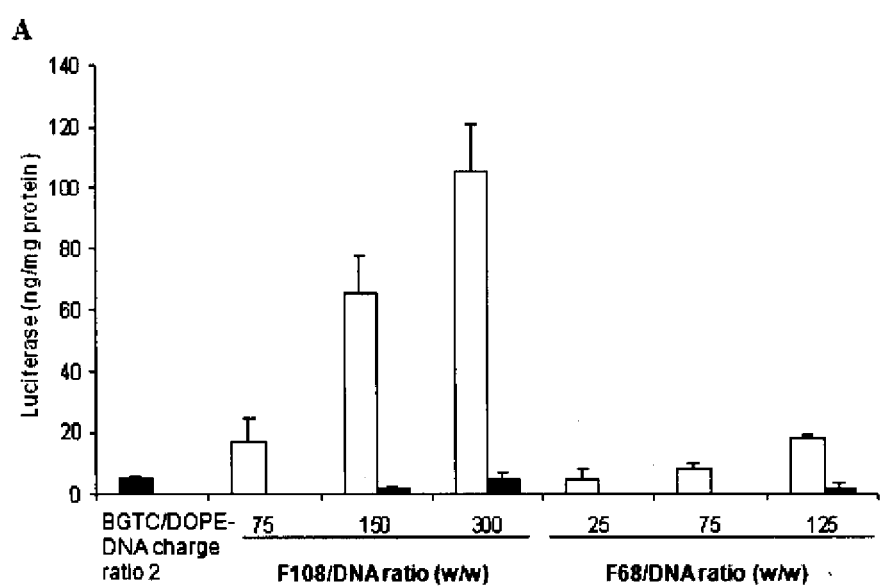

Attwood, D. et al., "Surfactant Systems," Pharmaceutical aspects of solubilization, 1983, pp. 356-361.

Kolb, H. et al., "Click Chemistry: Diverse Chemical Function from a Few Good Reactions," *Angew. Chem. Int. Ed.*, 2001, pp. 2004-2021, vol. 40.

Pitard, B. et al., "Negatively charged self-assembling DNA/poloxamine nanospheres for in vivo gene transfer," *Nucleic Acids Research*, 2004, pp. 1-8, vol. 32, No. 20.

Pitard, B. et al., "Structural characteristics of supramolecular assemblies formed by guanidinium-cholesterol reagents for gene transfection," *Proc. Natl. Acad. Sci. USA*, Mar. 1999, pp. 2621-2626, vol. 96.

Schiffelers, R. et al. "Cancer siRNA therapy by tumor selective delivery with ligand-targeted sterically stabilized Nanoparticle," *Nucleic Acids Research*, 2004, pp. 1-10, vol. 32, No. 19.

Pitard, B. et al., "Sterically stabilized BGTC-based lipoplexes: structural features and gene transfection into the mouse airways in vivo," *The Journal of Gene Medicine*, 2001, pp. 478-487, vol. 3.

Sagara, K. et al., "A new synthesis of galactose-poly(ethylene glycol)-polyethylenimine for gene delivery to hepatocytes," *Journal of Controlled Release*, 2002, pp. 271-281, vol. 79.

Letrou-Bonneval, E. et al., "Galactosylated multimodular lipoplexes for specific gene transfer into primary hepatocytes," *The Journal of Gene Medicine*, 2008, pp. 1198-1209, vol. 10.

International Search Report issued in International Application No. PCT/IB2009/053830 on Dec. 2, 2009.

Written Opinion of the International Searching Authority issued in International Application No. PCT/IB2009/053830 on Dec. 2, 2009.

International Preliminary Report on Patentability issued in International Application No. PCT/IB2009/053830 on Mar. 8, 2011.

\* cited by examiner

MULTIMODULAR ASSEMBLY USEFUL FOR INTRACELLULAR DELIVERY

The instant invention relates to non-viral stabilized multimodular assemblies useful for intracellular delivery of negatively charged macromolecules, and in particular of biological macromolecules. More particularly, the invention relates to stabilized multimodular assemblies useful for gene therapy and gene silencing.

Numerous non-viral cationic vectors or cationic transfection agents have been synthesized and are currently used for delivery of nucleic acids into cultured cells. The principle of non-viral gene delivery relies on the interaction of nucleic acids with cationic residues present on the vector through electrostatic forces.

The resulting cationic vector/DNA complexes display a three-stage model of colloidal stability depending on the theoretical charge ratio, corresponding to the moles of positive charges per mole of negative charges (phosphates). In zone A, for charge ratios below 1, negatively charged stable complexes are formed. In zone B, complexes precipitate as the charge ratio is close to neutral (ranging from 0 to 4, depending on the cationic lipid used and on the medium composition) due to the absence of electrostatic repulsion forces. In zone C (for charge ratios above 4), complexes are colloidally stable through electrostatic repulsion due to positively charged complexes. The most active complexes are those from zone C because their electrostatic interactions with negative molecules present at the cell surface lead to non-specific internalization through endocytosis, phagocytosis or macropinocytosis processes.

Whereas many cells types are transfected with cationic lipid/DNA lipoplexes using this principle, the excess of cationic lipid used to generate positively charged lipoplexes can lead to high cytotoxicity, compromising cell viability (Behr et al., *Proc Natl Acad Sci USA* 1989; 86: 6982; Felgner et al., *J Biol Chem* 1994; 269: 2550) and preventing specific transfection.

In this context, numerous strategies have been described to limit the cytotoxicity of positively charged complexes.

For example, it has been tried to substitute non-specific binding of positively charged particles to cells with a more specific interaction by a receptor-mediated process by using galactose molecule to target the asialoglycoprotein receptor (ASGR). Thus, galactose molecules were grafted onto different cationic vectors, including cationic lipids, polyethylene-imines (PEI) (Zanta et al., *Bioconjugate Chem* 1997; 8: 839), polylysine (PLL) (Nishikawa et al., *J Pharmacol Exp Ther* 1998; 287: 408) and peptides (Niidome et al., *Biomaterials* 2000; 21: 1811).

However, the presence of galactose in the cationic lipid led to only a modest increase in transfection compared to that obtained with cationic lipids without galactose. This is due to the still positive zeta potential of lipoplexes even with galactosylated cationic lipid, which lead to non-specific transfection. Besides, around neutrality, particles became much larger and unstable.

Furthermore, the presence of residual positive charges at the surface of galactosylated particles tends to show that complexes are internalized not only by receptor-mediated endocytosis, but also by non-specific endocytosis by electrostatic interactions.

It has also been suggested to decrease the charge ratio in the complexes (Remy et al., *Proc Natl Acad Sci USA* 1995; 92: 1744). Remy et al. describe the formation of particles resulting from the association of DNA with two independent molecules, i.e. cationic lipopolyamine and a galactosylated neutral lipid. However, the transfection activity of cationic vectors/DNA complexes was less efficient than positively charged complexes that did not contain galactosylated neutral lipid because they did not spontaneously internalize into cells by electrostatic interactions.

Besides, competition between the particles and asialofetuin, the natural ligand of ASPGR, in a transfection experiment, did not lead to a decrease in transgene expression, questioning the mechanism of transfection of the particles.

As other strategy, US 2005/0026287 has proposed the use of non-ionic surface active agent for stabilizing complexes of cationic transfection agent and nucleic acid. However, the transfection yield and specificity do not appear sufficient for a satisfying clinical outcome.

Therefore, there is still a need to have novel multimodular assemblies capable of specific intracellular delivery of negatively charged macromolecules, in particular of biological macromolecules.

There is a need for novel multimodular assemblies for use in gene therapy and gene silencing.

There is a need for novel multimodular assemblies useful for intracellular delivery and having low toxicity and high intracellular delivery yield.

There is also a need for novel multimodular assemblies having reduced size and improved stability.

There is also a need for novel multimodular assemblies useful for intracellular delivery and having the ability to comprise high content of negatively charged macromolecules and in particular of nucleic acid.

There is also a need for novel multimodular assemblies having the ability to selectively target specific cells or tissues.

There is also a need for novel multimodular assemblies, the ability of which to selectively target specific cell or tissue being able to be easily and handily tuned.

There is also a need for novel multimodular assemblies capable to increase the endosomal escape once the particles have been internalized through a specific receptor mediated endocytosis.

There is also a need for novel multimodular assemblies useful for vaccine composition.

The instant invention has for object to meet those needs.

The instant invention relates to a stabilized multimodular assembly useful for intracellular delivery comprising:
- a complex of at least one cationic transfection agent and of at least one negatively charged macromolecule, wherein said complex has a theoretical charge ratio ranging from about 0 to about 4, and
- an efficient amount of at least one amphiphilic block co-polymer acting as a steric colloidal stabilizer with respect to said complex, said amphiphilic block co-polymer comprising hydrophilic and hydrophobic blocks wherein at least one hydrophilic block is conjugated with at least one targeting ligand.

Unexpectedly, the inventors have observed that it was possible to obtain stable multimodular assemblies containing a condensed core of a negatively charged macromolecule, e.g. DNA, siRNA, or a mixture thereof surrounded by a corona of an amphiphilic block co-polymer functionalized with a targeting ligand, e.g. poly(ethylene oxide) stretches linked to hydrophobic moieties and functionalized with galactose at the distal ends, for cell recognition and internalization by a receptor-mediated process.

The instant invention further provides advantageously a simple and fast synthetic procedure to produce poly(ethylene oxide) hydrophobic derivatives containing galactose residues to target the asialoglycoprotein receptor (ASPGR) on primary hepatocytes.

The inventors have shown that it was possible to obtain stable complexes close to neutrality to avoid non-specific interaction with cell membranes, by forming small complexes resulting from the association of a cationic transfection agent, e.g. bis(guanidinium)-tren-cholesterol (BGTC)/dioleylphosphatidylethanolamine (DOPE) liposomes, or dioleyl succinyl paramomycin (DOSP)/DOPE liposomes or DOSP micelles, and a negatively charged macromolecule, e.g. DNA, at a theoretical charge ratio close to neutrality in the presence of an amphiphilic block co-polymer having at least one hydrophilic bloc end-conjugated with a targeting ligand, which serves both as a steric colloidal stabilizer and to target receptors.

The inventors have also shown that it is possible to prepare galactosylated multimodular lipoplexes by self-assembly of BGTC/DOPE or DOSP/DOPE liposomes, DOSP micelles, DNA or siRNA and steric colloidal stabilizer with chemical tunability.

As illustrated by the examples of the invention, the multimodular assemblies of the invention are efficient for specific and selective transfection of quiescent cells, such as primary hepatocytes in a specific manner and that non-equipped particles are totally inefficient.

The instant invention also relates to a vaccine composition comprising at least one multimodular assembly according to the invention.

Moreover, the instant invention relates to the use of at least one multimodular assembly according to the invention for the manufacture of a medicament intended to be used in gene therapy and gene silencing.

The invention also relates to the use of an efficient amount of at least one amphiphilic block co-polymer acting as a steric colloidal stabilizer, said amphiphilic block co-polymer comprising hydrophilic and hydrophobic blocks wherein at least one hydrophilic block is conjugated with at least one targeting ligand, in a multimodular assembly comprising a complex of at least one cationic transfection agent and at least one negatively charged macromolecule for increasing the cellular transfection yield.

Within the invention, the expression "negatively charged" with respect to the term "macromolecule" is intended to mean a molecule that comprise negative, and possibly positive, charges such that the total charge is negative and in an amount sufficient to allow interaction with the cationic transfection agent.

A multimodular assembly according to the invention may comprise at least one complexe of cationic transfection agents and of negatively charged macromolecules at theoretical charge ratio ranging from about 0.5 to about 3, in particular from about 1 to about 2.5, and more particularly being about 2.

In accordance with the invention, the implementation of complexes at a charge ratio close to neutrality leads to a colloidally unstable solution resulting in the formation of aggregates. The aggregation may be evidenced by precipitates visible to naked eyes.

Within the invention, the expression "efficient amount" is intended to mean the minimal amount necessary and sufficient to obtain a desired effect, as for example, in the context of the invention, the stabilization of a colloidal solution.

Within the invention, the expression "steric colloidal stabilizer" is intended to mean a compound able to interact with and to prevent the aggregation of particles or complexes thanks to a steric hindrance.

Within the invention, the terms "stabilized multimodular assembly" is intended to mean a particulate structure whose size is not likely to vary over time when, in particular, those particulate structures are maintained in dispersion in a solution. In other words, those particulate structures do not sensibly aggregate over a period of time.

Cationic Transfection Agent

A cationic transfection agent that may convene to the invention may be selected in the group consisting of cationic polymer and cationic lipid.

Within the invention, the terms "cationic lipid" intend to cover any compound or mixture with a lipid character and positively charged, already proposed as active agent with regard to the cellular transfection. In general, they are amphiphilic molecules comprising at least one lipophilic region combined or otherwise with a hydrophilic region.

A cationic lipid suitable for the invention may be constructed on the following model of structure: lipophilic group such hydrocarbon moieties combined through a so-called "spacer" arm with a cationic moiety including at least one nitrogen atom.

A cationic lipid in accordance of the invention may comprise as cationic moeity at least one ammonium and/or at least one guanidinium and/or at least amidinium group, or at least one aminoglycoside lipid derivative.

The hydrocarbon moieties of a cationic lipid useful for the invention may be derived from alkyl chain, fatty acid, fatty alcohol or fatty amine, in $C_8$-$C_{20}$, in particular in $C_{12}$-$C_{18}$, and more particularly in $C_{18}$.

For the purpose of the present invention, the term "aminoglycoside" (or "aminoside") is intended to mean a natural heteroside formed by the combining of a genin of the aminocyclitol group with generally several saccharides, at least one of which is anamino sugar (osamine). They may therefore be considered to be pseudooligosaccharides having antibiotic properties.

By way of example of suitable aminoglycosides, mention may be made of amikacin, arbekacin, deoxyhydrostreptomycin, destomycin 1, dibekacin, dihydrostreptomycin, genticin, gentamycin, hygromycin, isepamycin, kanamycin, micronomycin, paromomycin, ribostamycin, streptomycin, streptonicozide, neomycin, tobramycin, sisomycin or semi-synthetic aminosides.

According to a specific embodiment, an aminoglycoside suitable for the invention may be an aminoglycoside of the class of 4,5-disubstituted 2-deoxystreptamine ring.

The 4,5-disubstituted class includes neomycin, paromomycin, and ribostamycin, while the 4,6-disubstituted class includes tobramycin, kanamycine, amikacin and gentamycin.

In an embodiment a 4,5-disubstituted 2-deoxystreptamine aminoglycoside may advantageously be selected from paromomycin, neomycin, and ribostamycin, and preferably from paromomycin and neomycin. Alternatively, any synthetic or semi-synthetic 4,5-disubstituted 2-deoxystreptamine aminoglycoside may also be used.

The 4,5-disubstituted 2-deoxystreptamine aminoglycoside lipid derivatives are particularly useful for transfecting RNA and in particular siRNA.

The polyguanidylated derivative of an aminoglycoside according to the invention is the aminoglycoside for which the amino functions have been replaced with guanidinium functions. For example, the polyguanidylated derivative of kanamycin, or guanidinokanimycin, has been described by Baker et al. (J. Org. Chem., 2000, 65, pp. 9054-9058).

The term "spacer" represents a chemical group which makes it possible both to form the bond between for example the aminoglycoside or its polyguanidylated derivative and the lipophilic component of the molecule, and to distance these two components in order to reduce any undesired interaction between them.

A spacer suitable for the invention may be selected in the group consisting of alkyls having 1 to 6 carbon atoms, ketone, ester, ether, amino, amide, amidine, carbamate or thiocarbamate functions, glycerol, urea, thio-urea or aromatic rings.

According to one embodiment the lipophilic moiety may represent saturated or unsaturated alkyl radicals containing 10 to 22 carbon atoms and optionally containing one or more hetero atoms, provided that said fatty aliphatic chains have lipid properties.

They may be linear or branched alkyl radicals containing 10 to 22 carbon atoms and 1, 2 or 3 insaturations. The alkyl radicals may comprise 10, 12, 14, 16, 18, 20 or 22 carbon atoms. As examples, mention may be made of the aliphatic radicals $CH_3$.

According to another embodiment, the lipophilic moiety may derivate from polycyclic compounds of the cholestane type.

These compounds may or may not be natural and may be selected in the group consisting of cholesterol, cholestanol, 3-α-5-cyclo-5-α-cholestan-6-β-ol, cholic acid, cholesterol formiate, cholestanol formiate, 3-α-5-cyclo-5-α-cholestan-6-β-yl formiate, cholesterylamine, 6-(1,5dimethylhexyl)-3 α-5 α-dimethylhexadecahydrocyclopenta[a]cyclo-propa[2,3]cyclopenta[1,2-f]naphtalen-10-ylamine or cholestanylamine.

In particular, the lipophilic moiety represents a cholesterol radical.

In particular, an aminoglycoside lipid derivative may be selected in the group consisting of 3β[6'-kanamycincarbamoyl]cholesterol ("KanaChol"), 3β[6'-(1,3,3''-triguanidino) kanamycin-carbanoyl]cholesterol ("TGKC"), (5''-aminoethylsulfanyl)neomycin carbamoyl cholesterol, dioleylamine-A-succinyl-neomycine ("DOSN"), dioleylamine-A-succinyl-paromomycine ("DOSP"), NeoChol, NeoSucChol, ParomoChol, ParomoCapSucDOLA, ParomoLysSucDOLA, NeodiSucDODA, NeodiLysSucDOLA and [ParomoLys]$_2$-Glu-Lys-[SucDOLA]$_2$.

More particularly, the aminoglycoside lipid derivatives suitable for the invention are described in WO 03/018603 or in WO 2008/040792.

As other examples of suitable cationic lipid, one may mention those comprising, as lipophilic group, an hydrocarbon group such as fatty acid or cholesterol derivatives, and comprising, in addition, where appropriate, as amino group, a quaternary ammonium group, or a choline group.

Advantageously, a cationic lipid suitable for the invention may be chosen from lipopolyamines whose polyamine region corresponds to the general formula:

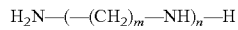

in which m is an integer greater than or equal to 2 and n is an integer greater than or equal to 1. It is possible for m to vary between the different groups of carbon between 2 amines.

In a lipopolyamine suitable for the invention, the polyamine region is covalently combined with a lipophilic region of the saturated or unsaturated hydrocarbon chain of cholesterol type, or a natural or synthetic lipid capable of forming lamellar or hexagonal phases. A polyamine region may be represented by spermine or one of its analogues which has conserved its nucleic acid-binding properties.

As examples of lipopolyamines suitable for the invention, one may mention the compounds described in EP 394 111. By way of representative of these lipopolyamines, one may mention more particularly dioctadecylamidoglycyl spermine (DOGS) and the palmitoylphosphatidylethanolamine 5-carboxyspermylamide (DPPES).

The lipopolyamines described in WO 96/17823 may also be used in the invention. By way of representative of these lipopolyamines, one may in particular mention 2,5-bis(3-aminopropylamino)pentyl (dioctadecylcarbamoylmethoxy) acetate and 1,3-bis(3-aminopropylamino)-2-propyl (dioctadecylcarbamoyl-methoxy)acetate.

Lipopolyamines described in WO 97/18185 may also convene to the invention. By way of representative of these lipopolyamines, one may more particularly mention {H$_2$N (CH$_2$)$_3$}$_2$N(CH$_2$)$_4$N {(CH$_2$)$_3$NH$_2$} (CH$_2$)$_3$NHCH$_2$COGlyN [(CH$_2$)$_{17}$CH$_3$]$_2$, H$_2$N(CH$_2$)$_3$NH(CH$_2$)$_4$NH(CH$_2$)$_3$ NHCH$_2$COGlyN[(CH$_2$)$_{17}$CH$_3$]$_2$, H$_2$N(CH$_2$)$_3$NH(CH$_2$)$_4$NH (CH$_2$)$_3$NHCH$_2$COArgN[(CH$_2$)$_{17}$CH$_3$]$_2$.

Cationic lipids incorporating one or more guanidinium and/or amidinium groups, such as more particularly those described by J. M. Lehn et al. (Proc. Natl. Acad. Sci. U.S.A, 1996, 93, 9682-9686) may also convene to the invention.

In a particularly advantageous manner, it is possible to use for the invention a cationic lipid selected in the group consisting of lipofectamine, dioctadecylamidoglycyl spermine (DOGS), palmitoylphosphatidylethanolamine 5-carboxyspermylamide (DPPES), 2,5-bis(3-aminopropylamino) pentyl(dioctadecylcarbamoylmethoxy)acetate, bis(guanidinium)-tren-cholesterol (BGTC), 1,3-bis(3-aminopropylamino)-2-propyl (dioctadecylcarbamoyl-methoxy)acetate, 1,2-dioleyloxy-3-trimethyl ammonium chloride propane (DOTAP), (N-(1-(2,3-dioleyloxy)propyl)-N,N,N-triméthylammonium chloride (DOTMA), N-[1]-(2,3-dimyristyloxy)propyl]N,N-dimethyl-N-(2-hydroxyethyl) ammonium chloride (DMRIE), 2,3-dioleyloxy-N-2-(carboxamidospermine)ethyl-N,N-dimethyl-1-propammonium chloride (DOSPA), DODAP (1,2-dioleoyl-3-(dimethylamino)propane), DODAB (dioctadecyldimethylammonium bromide), cetyl trimethylammonium bromide (CTAB), aminoglycoside lipide derivatives, such as 3β[6'-kanamycincarbamoyl]cholesterol ("KanaChol"), 3β[6'-(1,3,3''-triguanidino)kanamycin-carbanoyl] cholesterol ("TGKC"), (5''-aminoethylsulfanyl)neomycin carbamoyl cholesterol, dioleylamine-A-succinyl-neomycine ("DOSN"), dioleylamine-A-succinyl-paromomycine ("DOSP"), NeoChol, NeoSucChol, ParomoChol, ParomoCapSucDOLA, ParomoLysSucDOLA, NeodiSucDODA, NeodiLysSucDOAL and [ParomoLys]$_2$-Glu-Lys-[SucDOLA]$_2$, and mixtures thereof.

More particularly, a cationic lipid useful for the invention may be selected in the group consisting of BGTC, DOTAP, DOTMA, DMRIE, DOSPA, DOGS, DODAP, DODAB, CTAB, 1-DPPES, aminoglycoside lipid derivatives, such as KanaChol, TGKC, DOSN, or DOSP, and mixtures thereof.

According to an embodiment, a cationic lipid may be present in an amount ranging from 0.2% to 5%, in particular from 0.7% to 2.5%, and more particularly from 1% to 1.5% by weight relative to the total weight of a composition containing the multimodular assemblies of the invention.

According to one embodiment, a neutral lipid or co-lipid may be further mixed with a cationic lipid in multimodular assemblies of the invention.

A neutral lipid may be natural or synthetic lipid which is zwitterionic or which lack ionic charge under physiological conditions.

Neutral lipids or co-lipids that may convene for the invention may be selected in the group consisting of L-α-dioleylphosphatidylethanolamine (DOPE), dioleylphosphatidylcholine (DOPC), cholesterol, oleoylpalmitoylphosphatidylethanol-amine (POPE), distearoyl-, palmitoyl- and myristoylphosphatidylethanolamine as well as their 1- to 3-fold N-methylated derivatives; phosphatidylglycerols, diacylglycerols, glycosyldiacylglycerols, cerebrosides (such as, in particular, galactocerebrosides), sphingolipids (such as, in particular, shingomyelins) or alternatively asialogangliosides (such as, in particular, asialoGM1 and -GM2), and mixtures thereof.

According to one embodiment, DOPE, DOPC and POPE may be preferred.

According to an embodiment, a co-lipid may be present in an amount ranging from 0.2% to 1%, in particular from 0.3% to 0.8%, and more particularly from 0.5% to 0.6% by weight relative to the total weight of a composition containing the multimodular assemblies of the invention.

According to one embodiment, complexes of the invention may be prepared in particular with the following cationic lipid/neutral lipid pair: DOTAP/DOPE, BGTC/DOPE or DOSP/DOPE According to the present invention, a cationic polymer capable of being used as cationic transfection agent may be a polymeric compound including moieties of general formula as follows:

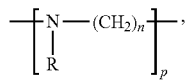

in which R may be a hydrogen atom or a group of formula:

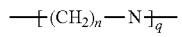

with n being an integer between 2 and 10, p and q being integers, it being understood that the sum p+q is such that the average molecular weight of the polymer is between 100 and $10^7$ Da.

It is understood that, in the formula above, the value of n may vary between the different units p. Thus, the formula groups may comprise together both homopolymers and heteropolymers. In the formula above, n is ranging from 2 and 5.

Cationic polymers that may convene according to the invention may be selected in the group consisting of polyethylene imine (PEI), polypropylene imine (PPI) and polylysine.

The polymers preferred for carrying out the present invention are those whose molecular weight is between $10^3$ and $5 \times 10^6$.

By way of example, one may mention the polyethylene imine of average molecular weight 20,000 Da (PEI20K), the polyethylene imine of average molecular weight 22,000 Da (PEI22K) or the polyethylene imine of average molecular weight 800,000 Da (PEI800K).

PEI25K, PEI22K and PEI800K are commercially available. Otherwise the polymers represented by the above formula may be prepared according to the process described in Patent Application FR 94/08735.

Amphiphilic Block Co-Polymer

A multimodular assembly of the invention comprises at least one amphiphilic block co-polymer that acts as a steric stabilizer in order to allow the stabilization of the complexes of the invention.

A stabilized multimodular assembly of the invention may comprise said amphiphilic block co-polymer and said negatively charged macromolecule in a weight ratio ranging from 10 to 1200, in particular from 55 to 800, and more particularly from 75 to 600.

The amount of amphiphilic block co-polymer that may be used to form a stabilized multimodular assembly of the invention is to be adapted according to the amount of complexes of cationic transfection agent and negatively charged macromolecule to be stabilized.

An amphiphilic block co-polymer of the invention may be present in amount ranging from 95% to 99.5%, in particular from 97% to 99%, and more particularly from 98% to 98.5% in weight with respect to the total weight of a composition comprising the stabilized multimodular assemblies of the invention.

According to one embodiment, in an amphiphilic block co-polymer useful for the invention the hydrophilic block may be selected in the group consisting of polyoxyalkylenes, polyvinyl alcohols, polyvinyl-pyrrolidones, poly(2-methyl-2-oxazoline), or saccharides, and the hydrophobic block that may be selected in the group consisting of polyoxyalkylenes, aliphatic chains, alkylidene polyesters, polyethylene glycol with a benzyl polyether head, and cholesterol.

Preferably, an amphiphilic block co-polymer that may be used within the invention is or comes from a nonionic polyol and more particularly from a polyoxyalkylene with alkylene groups of different lengths and/or conformations or otherwise within the polymer.

According to one embodiment, an amphiphilic block co-polymer may be selected in the group consisting of A-B or A-B-A type linear block co-polymers and (A-B)$_n$-C branched block co-polymers, with A representing an hydrophilic block, B representing an hydrophobic block, C representing a linking moiety, and n being 3 or 4 and figuring the number of (A-B) group linked to C.

In particular, the hydrophilic block A may be a polyoxyethylene block, the hydrophobic block B may be a polyoxypropylene block, the linking moiety C may be an ethylene diamine moiety, and n may be 4.

According to one embodiment, an amphiphilic block co-polymer that may be used in the invention may be a branched block co-polymer of the following formula:

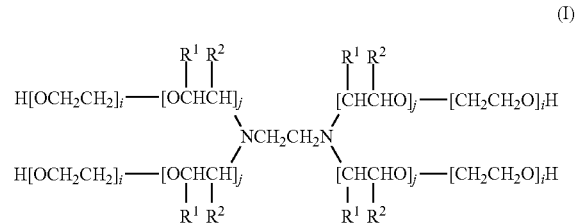

in which i has values from about 5 to about 125, in particular from about 10 to about 100, and j has values from 5 to about 25, in particular from about 10 to about 20, and more particularly equal to or greater than 13, and wherein for each $R^1$, $R^2$ pair, one shall be hydrogen and the other shall be a methyl group.

The diamine-linked pluronic of formula (I) can also be a member of the family of diamine-linked polyoxyethylene-polyoxypropylene polymers of formula:

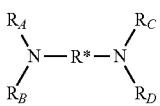

wherein $R_A$, $R_B$, $R_C$, $R_D$ represent independently of one another

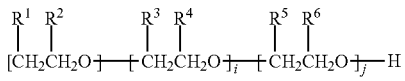

i and j are as above-described, R* is an alkylene of 2 to 6 carbons, a cycloalkylene of 5 to 8 carbons or phenylene, for $R^1$ and $R^2$, either (a) both are hydrogen or (b) one is hydrogen and the other is methyl, for $R^3$ and $R^4$ either (a) both are hydrogen or (b) one is hydrogen and the other is methyl, if both of $R^3$ and $R^4$ are hydrogen, then one $R^5$ and $R^6$ is hydrogen and the other is methyl, and if one of $R^3$ and $R^4$ is methyl, then both of $R^5$ and $R^6$ are hydrogen.

An amphiphilic branched block co-polymer of formula (I) may have a molecular weight ranging from 4000 to 35000 and in particular ranging from 4500 to 30000 and more particularly ranging from 5000 to 25000.

A branched block co-polymer with ethylene-oxide content greater than 40% and in particular greater than 60% or 80% may be especially preferred.

According to a preferred embodiment, an amphiphilic branched block co-polymer, and in particular a branched block co-polymer of the formula (I) or (II) as above described may be used with a complex consisting in one cationic lipid and one negatively charged macromolecule.

The cationic lipid may be in particular an aminoglycoside lipid derivative.

An amphiphilic block co-polymer that may be used in the invention may be:

an A-B-A type linear block co-polymer of formula:

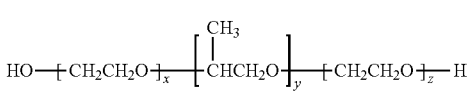

or an A-B type linear block co-polymer of formula:

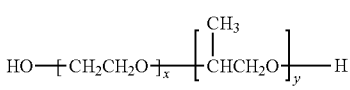

in which x and z have independently of each other values from about 100 to about 200, in particular from about 120 to about 180, and y have values from 35 to about 80, in particular from about 40 to about 60.

An amphiphilic linear block co-polymer of the invention may have a molecular weight ranging from 10 000 to 16 000, in particular from 11 000 to 15000, and more particularly from 11500 to 13000.

According to one embodiment, an amphiphilic linear block co-polymer of the invention may have an ethylene oxide content of greater than 50%, and especially of about 80%.

According to a preferred embodiment, an amphiphilic linear block co-polymer may be used with a complex consisting of one cationic lipid mixed with one co-lipid, and one negatively charged macromolecule.

Such poly(oxyethylene)-poly(oxypropylene) compounds have been described by Santon, Am. Perfumer Cosmet. 72(4): 54-58 (1958); Schmolka, Loc. cit. 82(7):25 (1967); Schick, Non-ionic Surfactants, pp. 300-371 (Dekker, N.Y., 1967), or in U.S. Pat. No. 6,353,055.

A number of such compounds are commercially available under such generic trade names as "poloxamers", "pluronics" and "synperonics".

The "polyoxamine" polymer of formula (III) is available from BASF (Wyandotte, Mich.) under the tradename Tetronic™.

Polyoxypropylene-polyoxyethylene block co-polymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block co-polymers are available from BASF under the tradename Pluradot™.

Block co-polymers that are especially suitable for use in the present invention include poloxamers 238 (F88), 288 (F98), 338 (F108), 407 (F127), 188 and poloxamine 704, 904, 908 and 1107.

Further details of suitable polyoxamers and poloxamines can be found in Surfactant Systems, Eds. Attwood and Florence, Chapman and Hall, London 1983, p 356-361; The Condensed Encyclopaedia of Surfactants, Ed. Ash and Ash, Edward Arnold, London, 1989 and Non-ionic Surfactants, Ed. Nace, Dekker, New York, 1996.

The amphiphilic block co-polymer of the invention may comprise at least one hydrophilic bloc end-conjugated with at least one targeting ligand as described thereafter.

Targeting Ligand

A stabilized multimodular assembly of the invention comprises one or more targeting elements or targeting ligands which make it possible to direct the complexes to specific binding elements or receptors at the surface of a cell.

By way of example, a targeting ligand suitable for the invention may be selected in the group consisting of monosaccharide or polysaccharide, RGD moiety, polylysine peptide, peptides, antibodies or fragments thereof, lectins, receptor ligands, growth factors, vitamins or cytokines As illustrative examples of useful targeting ligand for the invention, one may mention surfactant proteins A and B, artery wall binding peptide, asialoglycoproteins, lectins, anti-CD3 antibody, anti-CD5 antibody, hyaluronic acid fragments, steel factor or anti-CD117 antibody, EGF or EGF peptide receptor, anti-ErbB2 antibody, IgG, basic FGF, folate, malarial circumsporozoite protein, anti-HER2 antibody, insulin, RGD peptide, receptor associated protein (Rap), mannosylated synthetic ligands, NGF derived synthetic peptides, antibody ChCE7, antibody OV-TL16 Fab' fragment, anti-PECAM antibody, anti-secretory component, anti-IgG anti-idiotype antibody, anti-thrombomodulin, anti-Tn antibody, and transferin.

According to one embodiment, a targeting ligand suitable for the invention may be a galactose moiety.

According to one embodiment, at least 50%, in particular at least 70%, in particular at least 80% and more particularly at least 100% of said hydrophilic blocs of said amphiphilic block co-polymers are end-conjugated with a targeting ligand.

A surface density of targeting ligands of a multimodular assembly of the invention may be estimated on the basis of the proportion of hydrophilic block functionalized and upon the assumption of the amount of amphiphilic block co-polymer present per surface of the complex according to the formula (n/N)/S where n is the amount of amphiphilic block co-polymer in solution, N is the number of complexes in solution, and S is the surface of one complex.

A multimodular assembly according to the invention may have a surface density of targeting ligands ranging from 100 $nmol/cm^2$ to 800 $nmol/cm^2$, and in particular ranging from 200 $nmol/cm^2$ to 600 $nmol/cm^2$, and more particularly ranging from 300 $nmol/cm^2$ to 400 $nmol/cm^2$.

A targeting ligand may be attached to a hydrophilic block of a polymer of the invention according to any known technique in the art which is adapted according to the nature and to chemical properties of both the targeting ligand and the hydrophilic block.

According to one embodiment, a ligand may be attached to the free extremity of a hydrophilic block by enzymatic reaction or by chemical reaction.

The enzyme to be used in order to functionalize a terminal part of a hydrophilic block of an amphiphilic block co-polymer of the invention depends on the nature targeting ligand to be attached.

As example, when using galactose as a targeting ligand, an enzyme that may convene to the invention may be a galactosidase. In particular, the galactosidase from *Aspergillus oryzae* may convene to the invention.

According to another embodiment, a targeting ligand may be attached to the free terminal end of a hydrophilic block by a chemical reaction, and in particular by click-chemistry.

A click-chemistry reaction is a reaction between two functional moieties leading to the formation of at least one covalent binding between a carbon atom and an heteroatom.

Click-chemistry reactions that may be used in the invention are for example defined by Sharpless et al. (Angew Chem Int, 2001, 40, 2004-2021).

According to a preferred embodiment, functional moieties pair that may be used for the invention may be the nitrile or alcyne/azoture pair.

A click-chemistry reaction may be performed in presence of a catalyst. As useful catalyst, one may mention transition metal such as Cu.

As example of preferred chemical reaction useful for click-chemistry in accordance with the invention, one may mention the chemical reaction between an azide-functionalized compound and an alcyne-functionalized compound, in the presence of copper (Cu).

For instance, the amphiphilic block co-polymer of the invention may be functionalized with an azide moiety, whereas the targeting ligand to be attached to this amphiphilic block co-polymer may be functionalized with an alcyne moiety.

Negatively Charged Macromolecules

A stabilized multimodular assembly of the invention may comprise at least one negatively charged macromolecule.

A negatively charged macromolecule that may convene to the instant invention may be advantageously selected in the group consisting of nucleic acid, peptide nucleic acid, protein, antigen, and the like.

In a multimodular assembly of the invention, the nucleic acid complexed with the cationic transfection agent may be both a deoxyribonucleic acid and a ribonucleic acid.

These may be sequences of natural or artificial origin, and in particular genomic DNA, cDNA, mRNA, tRNA, rRNA, siRNA, miRNA, shRNA, hybrid sequences or synthetic or semisynthetic sequences of oligonucleotides, modified or otherwise.

These nucleic acids may be of human, animal, plant, bacterial or viral origin and the like. They may be obtained by any technique known to persons skilled in the art, and in particular by screening libraries, by chemical synthesis or alternatively by mixed methods including chemical or enzymatic modification of sequences obtained by screening libraries. They may be chemically modified.

As regards more particularly the deoxyribonucleic acids, they may be single- or double-stranded, as well as short oligonucleotides or longer sequences. These deoxyribonucleic acids may carry therapeutic genes, sequences for regulating transcription or replication, antisense sequences, modified or otherwise, regions for binding to other cellular components and the like.

For the purposes of the invention, therapeutic gene is understood to mean in particular any gene encoding a protein product having a therapeutic effect. The protein product thus encoded may be a protein, a peptide and the like. This protein product may be homologous with respect to the target cell (that is to say a product which is normally expressed in the target cell when the latter exhibits no pathology). In this case, the expression of a protein makes it possible, for example, to compensate for an insufficient expression in the cell or for the expression of a protein which is inactive or weakly active because of a modification, or alternatively to overexpress the said protein. The therapeutic gene may also encode a mutant of a cellular protein having increased stability, a modified activity and the like. The protein product may also be heterologous with respect to the target cell. In this case, an expressed protein may, for example, supplement or provide an activity which is deficient in the cell, allowing it to combat a pathology, or stimulate an immune response.

Among the therapeutic products for the purposes of the present invention, there may be mentioned more particularly enzymes, blood derivatives, hormones, lymphokines: interleukins, interferons, TNF and the like (FR 92/03120), growth factors, neuro-transmitters or precursors thereof or synthesis enzymes, trophic factors: BDNF, CNTF, NGF, IGF, GMF, aFGF, bFGF, NT3, NT5, HARP/pleiotrophin and the like, dystrophin or a minidystrophin (FR 91/11947), the protein CFTR associated with cystic fibrosis, tumour suppressor genes: p53, Rb, Rap1A, DCC, k-rev and the like (FR 93/04745), the genes encoding factors involved in clotting: factors VII, VIII and IX, the genes involved in DNA repair, suicide genes (thymidine kinase, cytosine deaminase), genes for haemoglobin or other carrier proteins, genes corresponding to the proteins involved in the metabolism of lipids, of the apolipoprotein type chosen from apolipoproteins A-I, A-II, A-IV, B, C-I, C-II, C-III, D, E, F, G, H, J and apo(a), metabolic enzymes such as for example lipoprotein lipase, hepatic lipase, lecithin cholesterol acyltransferase, 7-alpha-cholesterol hydroxylase, phosphatidic acid phosphatase, or alternatively proteins for transfer of lipids such as the protein for transfer of cholesterol esters and the protein for transfer of phospholipids, a protein for binding HDLs or alternatively a receptor chosen, for example, from the LDL receptors, receptors for remnant chylomicrons and scavenger receptors, and the like.

The therapeutic nucleic acid may also be a gene or an antisense sequence, whose expression in the target cell makes it possible to control the expression of genes or the transcription of cellular mRNAs. Such sequences may, for example, be transcribed in the target cell into RNAs complementary to cellular mRNAs and thereby block their translation into protein, according to the technique described in Patent EP 0 140 308. The therapeutic genes also comprise the sequences encoding ribozymes, which are capable of selectively destroying target RNAs (EP 0 321 201).

According to one embodiment the therapeutic nucleic acid may also be a siRNA, miRNA or shRNA, and in particular is a siRNA.

As example of useful siRNA one may mention the siRNA described in WO 2008/011431 that inhibit the expression of Proprotein Convertase Subtiliin Kexin 9 (PCSK9) genes, such as those PCSK9 genes associated with the development or maintenance of metabolic diseases traits and conditions, including but no limited to hyperlipidemia, hypercholesterolemia, cardiovascular disease, atherosclerosis, hypertension, diabetis (e.g. type I and/or type II diabetes), insulin resistance, obesity and/or any other diseases, traits, and conditions that are related to PCSK9 gene expression or activity.

As indicated above, the nucleic acid may also comprise one or more genes encoding an antigenic peptide capable of generating an immunoresponse in man or in animals. In this specific embodiment, the invention therefore allows the production either of vaccines or of immunotherapeutic treatments applied to man or to animals, in particular against microorganisms, viruses or cancers. This may be in particular antigenic peptides specific for the Epstein-Barr virus, the HIV virus, the hepatitis B virus (EP 0 185 573), the pseudorabies virus, the syncytia forming virus or other viruses, or alternatively specific for tumours (EP 0 259 212).

Preferably, the nucleic acid also comprises sequences allowing the expression of the therapeutic gene and/or of the gene encoding the antigenic peptide in the cell or desired organ. They may be sequences which are naturally responsible for the expression of the gene considered when these sequences are capable of functioning in the infected cell. They may also be sequences of different origin (responsible for the expression of other proteins, or even synthetic). In particular, they may be promoter sequences of eukaryotic or viral genes. For example, they may be promoter sequences derived from the genome of the cell which it is desired to infect. Likewise, they may be promoter sequences derived from the genome of a virus. In this regard, there may be mentioned, for example, the promoters of the E1A, MLP, CMV and RSV genes and the like. In addition, these expression sequences can be modified by the addition of activating or regulatory sequences and the like. The promoter may be inducible or repressible.

Moreover, the nucleic acid may also comprise, in particular upstream of the therapeutic gene, a signal sequence directing the therapeutic product synthesized in the secretory pathways of the target cell. This signal sequence may be the natural signal sequence of the therapeutic product, but it may also be any other functional signal sequence, or an artificial signal sequence. The nucleic acid may also comprise a signal sequence directing the therapeutic product synthesized to a specific compartment of the cell.

According to one embodiment, a negatively charged macromolecule may be present in an amount ranging from 0.15% to 2%, in particular from 0.3% to 1.5%, and more particularly from 0.6% to 1% by weight relative to the total weight of a composition containing the multimodular assemblies of the invention.

Multimodular Assembly

A multimodular assembly according to the invention may be obtained according to the following method.

From one hand, a solution of complexes of cationic transfection agent(s) and amphiphilic block co-polymer(s) functionalized with a targeting ligand is prepared at a concentration that is twice the concentration to reach in multimodular assemblies of the invention.

From another hand, a solution of negatively charged macromolecule(s) is prepared, at a concentration that is twice the concentration to reach in the mutimodular assemblies of the invention.

It is further proceeded to the mixing volume to volume of both previous solutions for obtaining the expected multimodular assemblies issued from the steric stabilization of the complexes. This solution of multimodular assemblies may be a saline solution comprising salts such as for example of NaCl at 150 mM or may be a medium for cell culture or a medium mimicking the extracellular ionic composition.

The complexes thus prepared have a theoretical charge ratio close to the neutrality, in particular ranging from about 0 to about 4. The theoretical charge ratio is corresponding to ratio of the mole of positive charges to the mole of negative charges.

The evaluation of the stability of a multimodular assembly in accordance with the invention may be performed as follows.

The stabilization of a multimodular assembly of the invention may be evaluated by dynamic light scattering for example with a Zetasizer 3000 HAS (Malvern). The measures are preferably made at 20° C. as described for example in Pitard et al. (*Nucleic Acid Res* 2004, 32: e159).

As observed by dynamic light scattering, the multimodular assemblies in accordance with the invention may present a mean diameter ranging from 200 to 500 nm, in particular ranging from about 300 to about 400 nm, and in particular being about 350 nm.

The multimodular assemblies of the invention present an improved stability over the time, for example ranging from 1 to 10 hours, and in particular from 2 to 5 hours.

The multimodular assemblies of the invention also present an improved stability in various medium conditions, ranging from simple saline solutions, for example comprising 150 mM NaCl, to complex cell culture mediums or medium mimicking the extracellular ionic composition.

The improved stability of the multimodular assemblies of the invention advantageously allows for shelf-storage over an extended period of time.

The improved stability of the multimodular assemblies of the invention advantageously renders them useful for in vivo administration, and in particular for administration in the blood stream where they display improved resistance over shear stress and prevent interaction with blood proteins such as albumin as well as complement proteins or cells of the mononuclear phagocyte system which participate in their destabilization and their removal from the blood.

As observed by microscopy in standard conditions in the field, the multimodular assemblies of the invention may advantageously be under the form of multilamellar liposome comprising DNA strands sandwiched between lipid bi-layer forming regularly repeated structures.

Pharmaceutical Compositions and Method of Treatment

The multimodular assemblies of the invention may be formulated in various compositions, and in particular in a pharmaceutical composition.

Therefore, the invention also relates to a composition, and more particularly to a pharmaceutical composition, comprising at least an effective amount of multimodular assemblies of the invention.

A pharmaceutical composition of the invention may comprise a vehicle that is pharmaceutically acceptable, in particular for an injectable formulation, in particular for systemic injection, injection directly into the desired organ or for topical administration, for example to the skin and/or mucous membranes. They may be sterile isotonic solutions or dry, in particular lyophilized, compositions which, by means of the addition, according to the case, of sterilized water or of physiological saline, make it possible to constitute injectable solutes.

It is clear that the doses of multimodular assemblies used for the injection and also the number of administrations may be adjusted by means of various parameters, and in particular as a function of the method of administration under consideration, of the pathology involved, of the nature of the negatively charged macromolecules to be administered, of the therapeutic or prophylactic effect to be reached, of the individual to be treated, and of the conditions to be treated or prevented.

For example, in the field of gene therapy, the doses of multimodular assemblies will depend of the gene to be expressed or repressed, or of the nature of the siRNA used to inhibit a gene expression.

Within the meaning of the invention, the term "to prevent" with respect to a disease is to be understood as meaning to reduce the risk of occurrence of said disease.

As regards more particularly the method of administration, it may involve either direct injection into the tissues or the circulatory system, or treatment of cells in culture followed by re-implantation in vivo by injection or graft.

A composition of the invention, comprising at least an effective amount of multimodular assemblies of the invention may prove to be particularly advantageous for internal administration.

For the purpose of the present invention, the term "internal administration" means that a composition of the invention is compatible with administration into the tissue of an organism, for example a muscle, intra-dermally or subcutaneously. Furthermore, topical, oral, pulmonary, nasal and mucosal, such as, for example, buccal, vaginal or rectal, administration may be used.

The compositions according to the invention are particularly advantageous from a therapeutic point of view, and in particular in gene therapy.

Thus, the potential applications are in the field of gene or antisense or gene silencing therapy.

Another application comes from the field of immunization. In this case, a nucleic acid, for example a DNA, encoding a bacterial, viral or other antigen is used to prepare the multimodular assemblies of the invention.

The multimodular assemblies thus prepared are then injected into cells, preferably muscle cells or dendritic cells.

Insofar as a composition of the invention is particularly advantageous for increasing the amount of proteins synthesized by the transfected cells, it is possible, by virtue of this, to obtain higher concentrations of antibodies and of cytotoxic T lymphocytes.

The invention also relates to a method for the intracellular delivery in vivo, and in particular transfection, of at least one negatively charged macromolecule, and in particular a nucleic acid sequence, characterized in that negatively charged macromolecule is administered within a multimodular assembly as above-defined to an individual in need thereof.

The administration can be carried out topically, directly into the cells under consideration, or by means of one of the routes of administration discussed above.

The present invention will be more fully described with the aid of the following examples and figures which should be considered as illustrative and nonlimiting.

FIGURES

FIG. 1 illustrates the transfection efficiency in primary hepatocytes of BGTC/DOPE-DNA/steric stabilizer lipoplexes as a function of the chemical structure of the steric stabilizer.

Two different amphiphilic block co-polymers with different chemical structures (F108, according to the invention, and F68, comparative polymer) were galactosylated and used for the formation of BGTC/DOPE-DNA lipoplexes at a theoretical charge ratio of 2 and containing 40 µg DNA/ml. The luciferase activity was assayed in transfected primary hepatocytes culture with galactosylated steric stabilizer (white bars) or ungalactosylated steric stabilizer (black bars).

Figure 2:
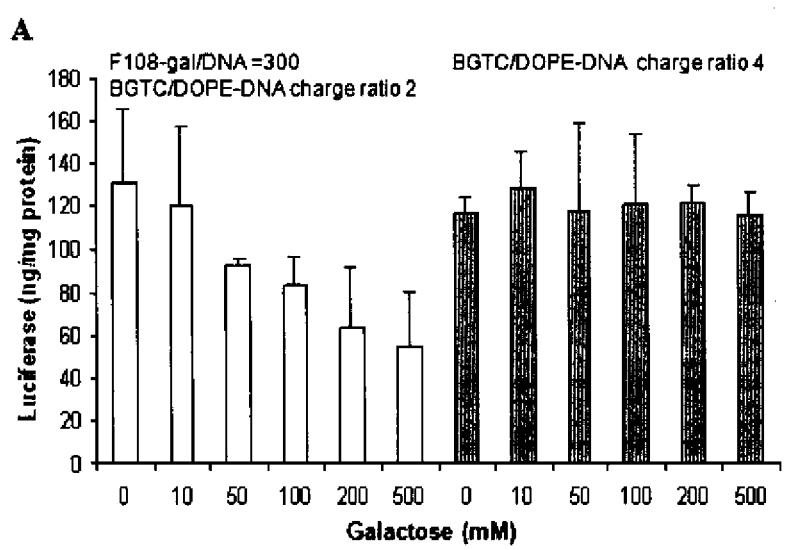

FIG. 2 illustrates specific in vitro transfection with BGTC/DOPE-DNA/F108-gal lipoplexes. The luciferase expression was assayed in primary hepatocyte cells transfected with BGTC/DOPE-DNA lipoplexes colloidally stabilized with F108-gal (F108-gal/DNA (w/w) ratio of 300) or with positively charged particles (BGTC/DOPE-DNA charge ratio of 4) as a function of the concentration of free galactose added to the cell culture medium 2 h before the transfection.

Figure 3:
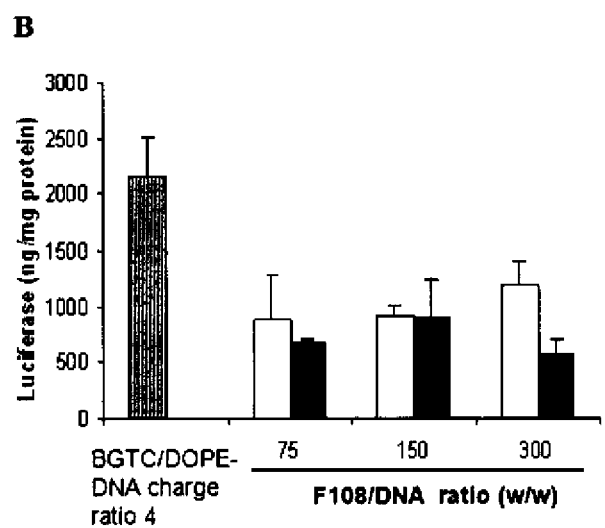

FIG. 3 illustrates specific in vitro transfection with BGTC/DOPE-DNA/F108-gal lipoplexes. The luciferase expression was assayed in Cos7 cells transfected with positively charged BGTC/DOPE-DNA lipoplexes or BGTC/DOPE-DNA lipoplexes at a BGTC/DOPE-DNA charge ratio of 4 formed in the presence of F108-gal (white bars) or F108 (black bars).

Figure 4:
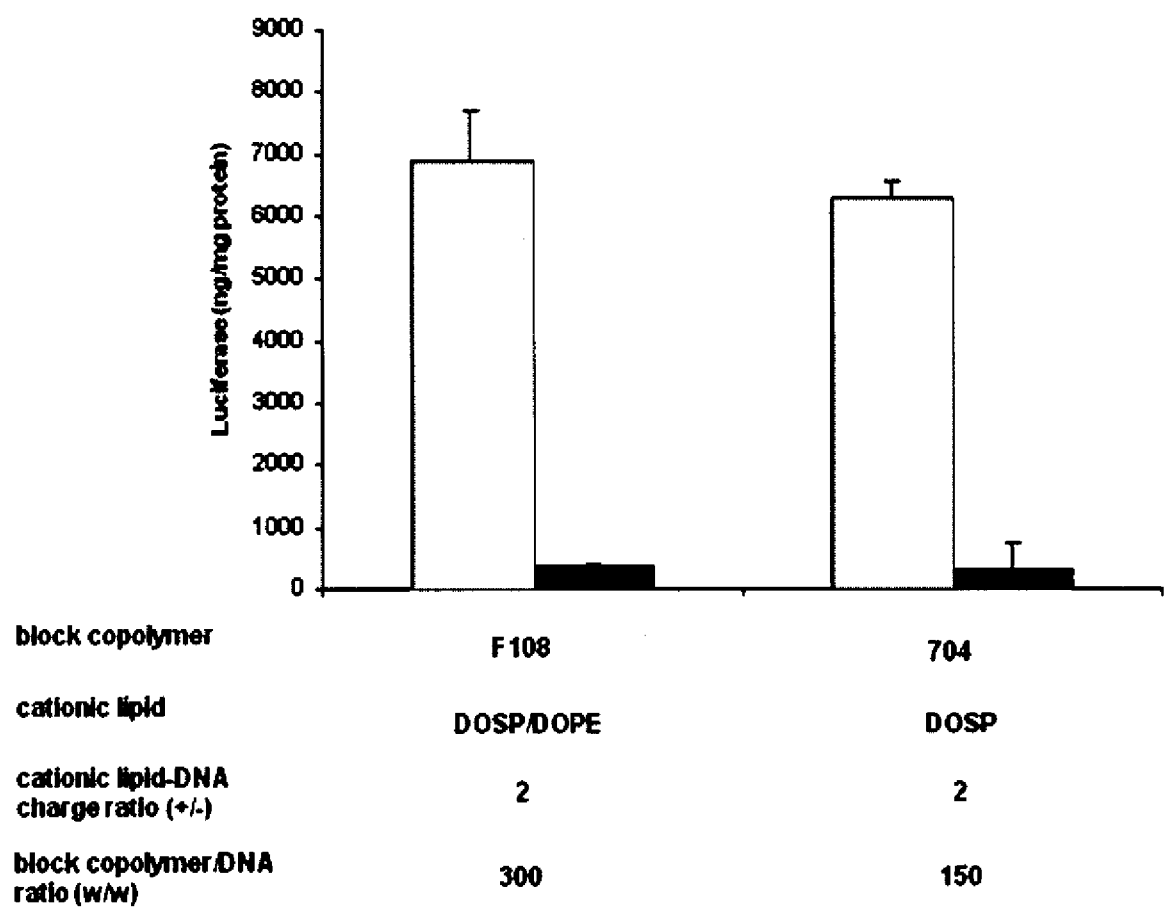

FIG. 4 illustrates the in vitro transfection efficiency in primary hepatocytes of DNA complexed with either cationic liposomes (at a charge ratio 2) of DOSP/DOPE in the presence of non-galactosylated (black bar) or galactosylated (white bar) linear block co-polymer type F108 (amphiphilic block co-polymer/DNA (w/w) at a ratio of 300) or DOSP micelles in the presence respectively of un-galactosylated (black bar) or galactosylated (white bar) tetrafunctionnalised block co-polymer type 704 (amphiphilic block co-polymer/DNA (w/w) at a ratio of 150).

Figure 5:
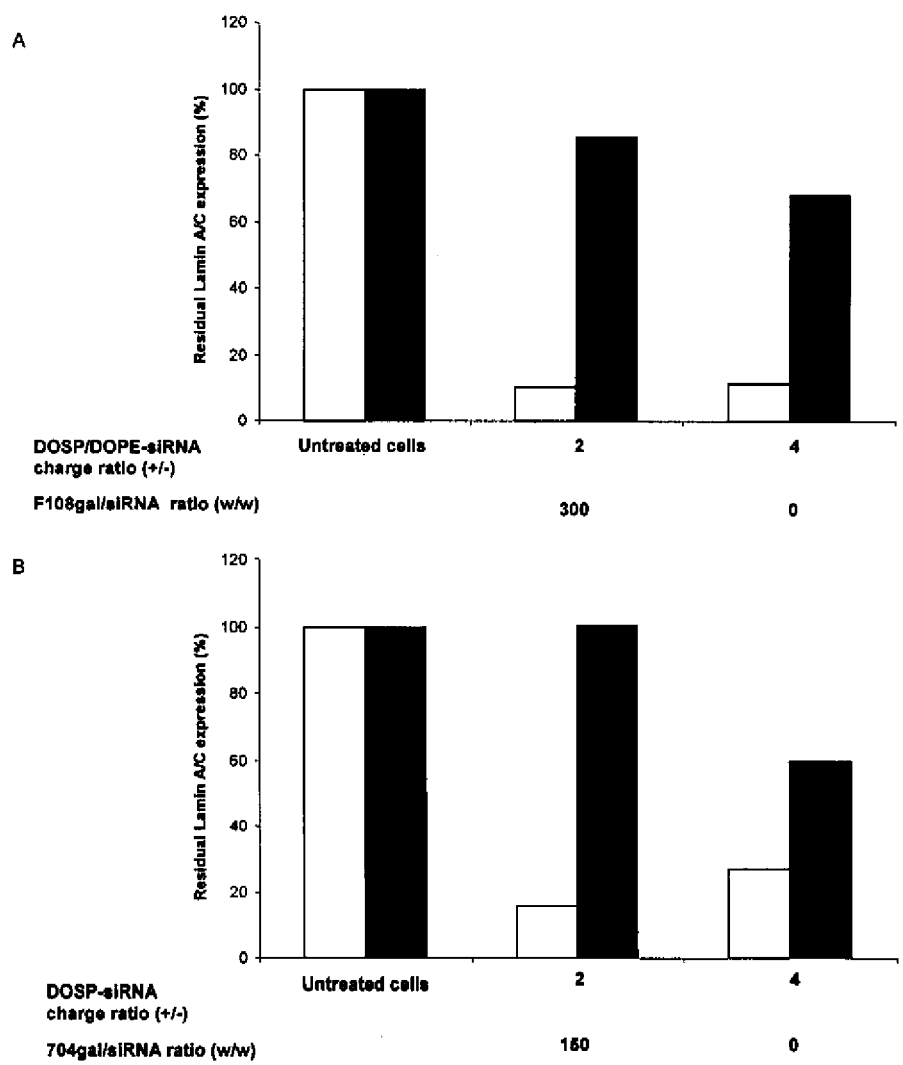

FIG. 5 illustrates the residual Lamin A/C expression after in vitro transfection of primary hepatocytes (white bars) and H1299 (black bars) cells with lipids-siRNA/galactosylated steric stabilizers complexes. Cells were transfected with 1.4 µg of anti-lamin A/C siRNA complexed with cationic liposomes of DOSP/DOPE (A) and with 2 µg of anti-lamin A/C siRNA complexed with DOSP micelles (B) at a charge ratio (+/−) of 2.5 and colloidaly stabilized, respectively, with F108-gal (F108-gal/siRNA ratio (w/w) of 300) and with 704-gal (704-gal/siRNA ratio (w/w) of 150). Positively charged ungalactosylated particles DOSP/DOPE-siRNA (A) and DOSP-siRNA (B) were also used as positive control. Residual lamin A/C expression was expressed as the ratio (%) of lamin A/C expression in cells transfected with siRNA control.

EXAMPLES

Example 1

Preparation of the Multimodular Assembly

Enzymatic Galactosylation of Amphiphilic Block Co-Polymers

The amphiphilic block co-polymers used as steric stabilizers for the study were F68 (80% poly(ethylene oxide); molecular weight (MW) 8400, comparative polymer) and F108 (80% poly(ethylene oxide), MW 14, 600, polymer of the invention), obtained from BASF. Stock solutions of steric stabilizers were prepared at given weight-to-weight (w/w) concentration in sterilized water and were kept at 4° C.

The synthesis of galactose-bearing F68 and galactose-bearing F108-gal was performed by first dissolving F68 and F108 (1 mM) in acetate buffer (100 mM, pH 4.5) and in N,N-dimethylformamide (10%). Then p-nitrophenyl β-D-galactopyranoside (pNP-β-gal) (Sigma-Aldrich; 2 mmol) was added at room temperature under vigorous stirring.

Finally, the β-galactosidase from *Aspergillus oryzae* (Sigma-Aldrich; 8.9 units) was added to the remaining solution, and the mixture was stirred for 15 h at 30° C.

The reaction was stopped by heating at 100° C. for 5 min, and the mixture was immediately dialyzed for 4 days under distilled water using a Pierce SnakeSkin® membrane (molecular weight cut-off (MWCO) 3500 Da). Then, the products were centrifuged, filtered with Amicon Ultra-15 centrifugal filter units (Millipore; MWCO 30.000 Da) and freeze-dried.

F68-gal: 1H NMR ($D_2O$): δ 4.30 (H1 gal, d, J=7.8 Hz), 3.78-3.73 ($CH_2$—$CH_2$—O—H, m), 3.67-3.40 (bs, ($CH_2$—$CH_2$—O)$_n$, (—O—$CH_2$—CH—($CH_3$)—O)$_n$), 1.06-1.03 (m, (—O—$CH_2$—CH—($CH_3$)—O)$_n$).

F108-gal: $^1$H NMR ($D_2O$): δ 4.30 (H1 gal, d, J=7.8 Hz), 3.80-3.75 ($CH_2$—$CH_2$—O—H, m), 3.67-3.29 (bs, ($CH_2$—$CH_2$—O)$_n$, (—O—$CH_2$—CH—($CH_3$)—O)$_n$), 1.09-1.06 (m, (—O—$CH_2$—CH—($CH_3$)—O)$_n$).

The average number of galactose units grafted onto steric stabilizers was determined by the ratio of the anomeric signal of galactose (1H, H1 gal, 4.30 ppm, d, J=7.8 Hz) and the chemical shifts of non-modified terminal methylenes (4H, $CH_2$—$CH_2$—O—H, 3.75-3.80 ppm m) of amphiphilic block co-polymers.

This calculation indicated that around 25% of the terminal OH groups of the F108 and F68 steric stabilizers were linked to β-galactose.

Preparation of Lipoplexes

A plasmid encoding the luciferase reporter gene under the control of the human cytomegalovirus immediate-early gene promoter, pCMV-Luc, was used as DNA. Plasmid was purified from recombinant *E. coli* by means of Endofree plasmid purification columns (Qiagen, Chatsworth, Calif., USA).

BGTC/DOPE liposomes were obtained as previously described in Pitard B, et al., *Proc Natl Acad Sci; USA* 1999; 96: 2621.

Formulations of DNA with BGTC were prepared by mixing equal volumes of desired concentrations of BGTC/DOPE liposomes with plasmid DNA at the desired concentration. Formulations of DNA complexes with F108, F108-gal or F68, F68-gal were prepared by mixing solutions of cationic liposomes containing required concentrations of steric stabilizers with plasmid DNA solution.

The galactose density at the surface of BGTC/DOPE DNA/F108-gal lipoplexes was estimated by assuming that the amount of steric stabilizer present per surface unit of lipoplex was 338 nmol/$cm^2$, according to the formula (n/N)/S, where n is the amount of steric stabilizer in solution (40.6 nmol), N is the number of lipoplexes in solution (1.25×108), and S is the surface of one lipoplex (9.6×$10^{-10}$ $cm^2$.) Therefore, these lipoplexes contained 135 nmol galactose/$cm^2$. This value was in good agreement with a previously described system characterized by a similar galactose density which enabled the binding of ASPGR of primary hepatocytes with a high affinity.

Example 2

Structural Features of the Multimodular Assemblies

Dynamic Light Scattering, Fluorescence and Cryo-TEM Studies

Dynamic light scattering measurements were made on a Zetasizer 3000 HSA (Malvern) at 20° C. (Pitard B, et al., *Proc Natl Acad Sci; USA* 1999; 96: 2621).

Samples were prepared by complexing DNA with BGTC/DOPE liposomes at a charge ratio of 2 and with F108-gal or F108 at various w/w ratios. Formation of complexes was confirmed by electrophoresis on 1.0% agarose gel with Tris-acetate running buffer at 100 V for 20 min.

Multimodular lipoplexes were assembled by condensing DNA molecules with BGTC/DOPE liposomes at a charge ratio close to neutrality in the presence of F108-gal, or F108. The influence of the amphiphilic block co-polymers/DNA ratio on the colloidal stability of the BGTC/DOPE-DNA/F108-gal lipoplexes and the BGTC/DOPE-DNA/F108 lipoplexes was examined. To this end, the mean particle diameter was measured by dynamic light scattering. The mean diameter of BGTC/DOPE-DNA lipoplexes at a charge ratio of 2 as a function of F108-gal/DNA ratio and F108/DNA ratio was measured.

In the absence of amphiphilic block co-polymers and at this low ratio, colloidally unstable lipoplexes were obtained, as evidenced by visible precipitates which cannot be measured by dynamic light scattering.

Under this condition an arbitrary value of 700 nm was attributed for those non-colloidally stable lipoplexes. By contrast, addition of F108 allowed the formation of stable DNA complexes with a mean diameter of 150 nm at an F108/DNA ratio starting from 100. F108-gal led also to the formation of colloidally stable BGTC/DOPEDNA lipoplexes with a mean diameter of 300 nm starting from an F108-gal/DNA ratio of 300. Fluorescence experiments, performed by exposing BGTC/DOPE-DNA/F108-gal lipoplexes and BGTC/DOPE-DNA/F108 lipoplexes to ethidium bromide, showed that the fluorescence level was very low. This indicates that all DNA molecules were totally incorporated into BGTC/DOPE-DNA particles even stabilized by F108-gal or F108.

The influence of the BGTC/DOPE-DNA charge ratio on the mean diameter of complexes and the DNA complexation in the presence of F108-gal or F108 was also studied. DNA complexed by BGTC/DOPE liposomes in the presence of F108-gal and F108 led to the formation of particles of a mean diameter of about 350 and 220 nm, respectively, irrespective of the BGTC/DOPE-DNA charge ratio.

By contrast parallel experiment performed with F68-gal revealed that this modified block co-polymer does not allow to colloidally stabilized particles with galactosylated moiety grafted at the distal extremity of the F68.

Size Determination of Complexes in Transfection Media

BGTC/DOPE-DNA/F108-gal lipoplexes prepared at a charge ratio of 2 and at an F108-gal/DNA ratio (w/w) of 300 and BGTC/DOPE-DNA lipoplexes at a charge ratio of 4 were formed in 150 mM NaCl by mixing 50 μl of F108-gal or BGTC/DOPE solutions with 50 μl (200 μg/ml) plasmid DNA.

Samples were analyzed after 20 min of complexation at room temperature. Just prior to dynamic light scattering analysis, 1000 μl of either 150 mM NaCl or Dulbecco's modified Eagle's medium (DMEM) (plus additives used for culturing primary hepatocytes) was added to lipoplexes.

Size determination was obtained every hour for lipoplexes diluted with NaCl or DMEM.

Dynamic light scattering analysis of lipoplexes provides a means of checking for the colloidal stability of particles destined for in vitro transfection. However, measurement of particle size alone does not take into account possible transfection medium-induced effects on the size of the complexes. In fact, it is possible that charged species in the medium could alter the size of preformed lipoplexes before effective transfection takes place.

To address this issue, preformed lipoplexes representing both BGTC/DOPE-DNA/F108-gal lipoplexes prepared at a charge ratio of 2 and at an F108-gal/DNA ratio of 300, and BGTC/DOPE-DNA lipoplexes at a charge ratio of 4, were evaluated either in the transfection medium of primary hepatocytes or in 150 mM NaCl solution. Results from dynamic light scattering analysis performed every hour on the lipoplexes show that, within 1 h of adding transfection medium, the size of lipoplexes at a BGTC/DOPE-DNA charge ratio of 4 began to increase until aggregates were formed.

By contrast, BGTC/DOPE-DNA/F108-gal lipoplexes were able to maintain their small size in saline solution as well as in transfection medium.

Example 3

Cell Transfection

Primary Culture of Hepatocytes

Hepatocytes were isolated from the liver of fed male rats or mice by the collagenase method (Berry et al., *J Cell Biol* 1969; 43: 506), modified as described elsewhere (Balavoine et al., *J Cell Physiol* 1993; 156: 56). Briefly, livers were perfused with Hank's balanced salt solution, and washed at a rate of 5 ml/min using the inferior veina cava before collagenase (0.025%) was added. Dead cells were eliminated through a density gradient using percoll, and viable cells were plated at a density of 75 000/cm2 on collagen-coated plates. Cells were given a time span of 2 h to attach in William's medium E with Glutamax (Invitrogen), 10% fetal bovine serum (FBS), 10 µg/ml streptomycin, 100 u/ml penicillin, 100 nM dexamethasone and 100 nM insulin (Actrapid, Novo Nordisk, Bagsvaerd, Denmark).

Cell Line Culture

Cos7 green monkey kidney fibroblast cells were grown in high glucose DMEM (Invitrogen) (4.5 g/l). Cell culture media were supplemented with 10% FBS, 2 mM L-glutamine, 10 µg/ml streptomycin, 100 u/ml penicillin at 37° C. under humidified 5% $CO_2$. Cells were plated at a density of 35 000/cm$^2$ 24 h prior to transfection.

Culture Cell Transfection

Cells were transfected with BGTC/DOPE-DNA lipoplexes formulated at BGTC/DOPE-DNA charge ratios of 4 or 2 in the presence of F108-gal, F108 or F68-gal, F68 at various amphiphilic block co-polymers/DNA ratios.

BGTC/DOPEDNA/amphiphilic block co-polymers lipoplexes containing 2 µg of luciferase plasmid were added to each well. Lipoplexes were incubated at room temperature for 15-20 min before transfection. After transfection (4 h), the serum free medium (300 µl) was then replaced with 1 ml of growth medium containing 10% FBS for Cos7 and without FBS for primary hepatocytes. Cells were cultured for an additional 20 h before gene expression was determined.

Luciferase Assay

Luciferase activity was measured using the Promega luciferase assay system (Madison, Wis., USA). Cells were rinsed twice with 500 µl of phosphate-buffered saline (PBS) and lysed with 200 µl of reporter lysis buffer (Roche Diagnostics, Mannheim, Germany) supplemented with a protease inhibitor cocktail (Roche Diagnostics).

Then, strictly hepatocyte cells were subjected to four freeze/thaw cycles. After 5 min of centrifugation at 10 000 rpm and 4° C., luciferase activities were measured from an aliquot of supernatant with a VICTOR multilabel counter (Perkin Elmer, Les Ulis, France).

Luciferase activity was assayed by measuring light emission after addition of 100 µl of luciferase substrate to 20 µl of the supernatant. Protein content was measured with a bicinchoninic acid (BCA) protein assay kit.

Results

Primary hepatocyte cells were transfected with BGTC/DOPE-DNA lipoplexes formulated at a BGTC/DOPE-DNA charge ratio of 2 in the presence of F108-gal and F108 or F68-gal and F68 at various amphiphilic block co-polymers/DNA ratios.

FIG. 1 shows that DNA complexes formulated with F108-gal led to a dramatic increase in luciferase expression as the F108-gal/DNA ratio increased. Whereas F68-gal led to a marked lower luciferase expression and very low difference in luciferase expression between galactosylated and ungalactosylated particles. Furthermore, BGTC/DOPE-DNA lipoplexes formed in the absence or presence of ungalactosylated F108 or F68 did not lead to significant primary hepatocyte transfection.

Therefore, these results strongly suggest that particles equipped with galactose lead to specific hepatocyte transfection and that the length of the functionalized hydrophilic bloc of the amphiphilic block co-polymers plays a role both in the formation of supramolecular assemblies and in the accessibility of the ligand for the receptor-mediated endocytosis pathway.

Further experiments were performed with particles characterized by an F108/DNA ratio of 300. Next, experiments were undertaken to determine the optimal BGTC/DOPE-DNA charge ratio that allowed the highest luciferase activity with BGTC/DOPE-DNA/F108-gal lipoplexes.

The obtained results indicate that BGTC/DOPE-DNA/F108-gal lipoplexes formulated at a BGTC/DOPE-DNA charge ratio of 2 gave the highest transfection efficiency. In this experiment ungalactosylated lipoplexes did not transfect primary hepatocytes.

To demonstrate the cell-specific transfection with galactosylated multimodular lipoplexes, experiments on primary hepatocytes in the absence and presence of various concentrations of free galactose, which can bind to the ASGPR were carried out (FIG. 2). This experiment was also performed with BGTC/DOPE-DNA lipoplexes formed at a charge ratio of 4 as control because these positively charged lipoplexes should not be internalized through ASPGR but rather through electrostatic interactions.

In the absence of free galactose, BGTC/DOPE-DNA/F108-gal lipoplexes at an F108-gal/DNA ratio of 300 formulated with BGTC/DOPE-DNA at a charge ratio of 2 gave a similar activity to BGTC/DOPE-DNA lipoplexes at a charge ratio of 4 (FIG. 2), indicating that the natural receptor mediated internatization was as efficient as the un-natural internalization through electrostic interaction between positively charged particles and negatively charged molecules present at the surface of the cell membrane.

The increasing of the concentration of free galactose led to a progressive decrease in luciferase expression. By contrast, as expected the presence of free galactose did not affect the luciferase activity of highly positively charged lipoplexes (FIG. 2).

Consequently, these results show that competition takes place between galactosylated multimodular lipoplexes and free galactose to interact with ASPGR, suggesting that BGTC/DOPE-DNA/F108-gal lipoplexes are internalized in primary hepatocytes by a receptor-mediated process.

To confirm the specific effects of BGTC/DOPE-DNA/F108-gal lipoplexes on receptor-mediated transfection, control experiments on Cos7 cells, which do not express ASGPR were carried out. The transfection efficiency of lipoplexes colloidally stabilized with F108-gal or F108 was similar and lower than that observed with positively charged BGTC/DOPE-DNA lipoplexes (FIG. 3).

To confirm the receptor-mediated endocytosis pathway for transfection of BGTC/DOPE-DNA/F108-gal lipoplexes, primary hepatocyte cells were transfected after pre-incubation with nocodazole, which induces depolymerization of microtubules. Nocodazole inhibits transport of endosomal vesicles from early to late endosomes. This chemical substance prevents lysosomal degradation so nocodazole improves one step of the endocytosis process. Nocodazole pre-treatment increased the transfection efficiency of BGTC/DOPE-DNA/F108-gal lipoplexes.

By contrast, in the presence or absence of nocodazole, BGTC/DOPE-DNA lipoplexes at a charge ratio of 4 gave similar levels of luciferase expression (data not shown). Therefore, BGTC/DOPE-DNA lipoplexes at a charge ratio of 4 are mainly internalized by non-specific electrostatic interactions with the cellular membrane, although BGTC/DOPE-DNA/F108-gal lipoplexes transfected through an endocytosis process.

Example 4

Cell Transfection Using Aminoglycoside Lipid Derivative 704 is a tetrafunctionnalized amphiphilic block co-polymer (molecular weight (MW) 5500, 40% poly(ethylene oxide)). The 704 was galactosylated according to the following method.

2,3,4,6-Tetra-O-acetyl-α-D-galactopyranosyl trichloroacetamidate

Under nitrogen atmosphere, hydrazine acetate (197 mg, 2.19 mmol, 1.4 equiv) was added to a solution of β-D-galactopyranose pentaacetate (605 mg, 1.55 mmol) in anhydrous THF (10 mL) in presence of 4 Å molecular sieve. The reaction mixture was stirred at room temperature for 4 h 30, filtered, concentrated to dryness under reduced pressure and purified by chromatography on silica gel (25:1, dichloromethane/methanol) to afford 2,3,4,6-tetra-O-acetyl-D-galactopyranose (528 mg, 98%) as a yellow oil which was directly used in the next step. Under nitrogen atmosphere, trichloroacetonitrile (1.34 mL, 13.4 mmol, 8.8 equiv) and potassium carbonate (1.42 g, 10.3 mmol, 6.7 equiv) were added to a solution of 2,3,4,6-tetra-O-acetyl-D-galactopyranose (528 mg, 1.52 mmol) in anhydrous dichloromethane (20 mL) in presence of 4 Å molecular sieve. The reaction mixture was vigourously stirred at room temperature for 12 h, filtered and concentrated to dryness under reduced pressure to afford 2,3,4,6-tetra-O-acetyl-α-D-galactopyranosyl trichloroacetamidate (707 mg, 95%) which was used without further purification.

Tetra-O-acetate galactosylated 704 bloc copolymer: 704-GalAc$_4$

Under nitrogen atmosphere, boron trifluoride ethyl etherate (100 μL, 790 μmol, 25 equiv) was added at room temperature to a solution of tetronic 704 (175 mg, 32 μmol) and 2,3,4,6-tetra-O-acetyl-α-D-galactopyranosyl trichloroacetamidate (157 mg, 320 μmol, 10 equiv) in anhydrous dichloromethane (15 mL) and the reaction mixture was stirred at room temperature for 2 h. The solution was concentrated under reduce pressure, diluted with phosphate buffer (pH 7, 4 mL) and purified by dialysis (Cellu•Sep® H1 dialysis membrane 2,000 MCWO) against MilliQ deionized water (6×1.5 L) at 4° C., followed by lyophilisation to afford 704-GalAc$_4$ as a yellow oil (201 mg, up to 75% of acetylated galactose incorporation).

Galactosylated 704 bloc copolymer: 704-Gal

704-GalAc$_4$ (316 mg, 46 μmol) was dissolved in a freshly prepared methanolate solution (200 mM, 3.16 mL, 632 μmol, 14 equiv) and the solution was stirred at room temperature for 2 h. The solution was concentrated under reduce pressure, diluted with phosphate buffer (pH 7, 3 mL) and purified by dialysis (Cellu•Sep® H1 dialysis membrane 2,000 MCWO) against MilliQ deionized water (6×1.5 L) at 4° C., followed by lyophilisation to afford 704-Gal as a yellow oil (233 mg, quantitative conversion, up to 75% of galactose incorporation).

Multimodular assemblies were prepared with said galactosylated and a non-galactosylated amphipilic polymer.

The multimodular assemblies complexing a plasmid encoding the luciferase gene reporter at a theoretical charge ratio of 2 were obtained as described in example 1 except that BGTC was replaced by the aminoglycoside lipid derivative DOSP and that the multimodular assemblies with 704 or 704-gal were prepared without the co-lipid DOPE.

In the multimodular assemblies DOSP/DOPE-pCMV-Luc/F108 or F108-gal, the ratio DNA/F108 was 300.

In the multimodular assemblies DOSP-pCMV-Luc/704 or 704-gal, the ratio DNA/704 was 150.

Primary culture of hepatocytes and cell transfection were performed according to the conditions and the protocols described in examples 1 and 3.

The luciferase assay was performed as described in example 3.

The results shown in FIG. 4 indicate that no cell transfection occurred when carried out with multimodular assemblies prepared with non-galactosylated amphiphilic block co-polymer (black bar) and that the aminoglycoside lipid derivative used alone with 704-gal was as efficient as the combination aminoglycoside lipid derivative/neutral lipid-F108-gal (white bar).

Example 5

Gene Silencing

In this experiment the F108-gal and 704-gal multimodular assemblies were as described in Example 4, except that the pCMV-Luc plasmid was replaced by a human anti-lamin A/C siRNA obtained from Santa Cruz Biotechnology (Santa Cruz, Calif., USA).

Primary hepatocytes cell culture and transfection were performed as described in Example 3.

HeLa cells were cultured in standard in DMEM conditions and transfected as the hepatocytes cells. HeLa cells were used as control cells because they do not express the asialoglycoprotein receptors which recognize galactose for specific delivery of siRNA.

Cells were transfected with 37.5 ng of anti-lamin A/C siRNA in mixture with 2 μg of DNA as plasmid carrier.

Twenty-four after incubation, gene-silencing of lamin A/C expression obtained on primary hepatocytes was compared to HeLa cells.

The residual lamin A/C expressions were determined by real-time quantitative RT-PCR.

The real-time quantitative RT-PCR was performed as followed: total RNA was extracted from transfected cells by Trizol treatment. Reverse transcription was performed with total RNA using oligo(dT)20 primers and SuperScript III reverse transcriptase (Invitrogen). The expression of Lamin A/C was quantified by real-time PCR (ABI prism 7000, Applied Biosystems).

Experiments were performed using PCR Master Mix (Applied Biosystems) with 300 nM of each primer (Lamin A/C reference Applied Biosystems Rn00572764-m1, and HPRT1 reference Applied Biosystems Rn01527840-m1) and 250 nM of TaqMan MGB probes. Primers were obtained from Applied Biosystems. The cycling conditions included a hot start at 95° C. for 10 min, followed by 40 cycles at 95° C. for 15 s and 60° C. for 1 min.

Results were normalized to the endogenous Hypoxanthine-guanine phosphoribosyltransferase (HPRT1) control gene and expressed according to the $2^{-\Delta CT}$ method.

The results show that in HeLa cells not expressing the ASGR, no inhibition of the A/C lamin expression occurs, whereas in hepatocytes cells the expression is drastically reduced.

Example 6

The experiment of example 5 is reproduced with only siRNA i.e. without plasmid carrier and by using H1299 cells as controlled cells because they do not express the asialoglycoprotein receptors which recognize galactose for specific delivery of siRNA.

The results submitted in FIG. 5 show that in H1299 cells (black bar) not expressing the ASGR, no inhibition of the A/C lamin expression occurs, whereas in hepatocytes cells (white bar) the expression is drastically reduced.

The invention claimed is:

1. A stabilized multimodular assembly useful for intracellular delivery comprising:
    a complex of at least one cationic transfection agent and of at least one negatively charged macromolecule, wherein said complex has a theoretical charge ratio ranging from about 0 to about 4, the theoretical charge ratio being defined as a number of moles of positive charges per mole of negative charges, and
    an efficient amount of at least one amphiphilic block co-polymer acting as a steric colloidal stabilizer with respect to said complex, said amphiphilic block co-polymer comprising hydrophilic and hydrophobic blocks wherein at least one hydrophilic block is conjugated with at least one targeting ligand, and wherein said amphiphilic block co-polymer is an A-B-A type linear block co-polymer of the following formula (III) or formula (IV):

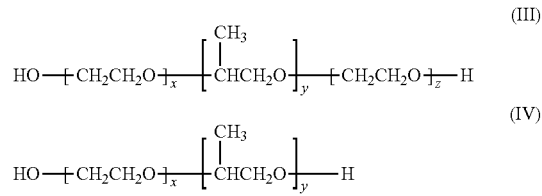

in which x and z have, independently of each other, a value from about 100 to about 200, and y has a value from 35 to about 80.

2. The multimodular assembly according to claim 1, wherein the cationic transfection agent is selected from the group consisting of cationic polymer and cationic lipid.

3. The multimodular assembly according to claim 2, wherein said cationic lipid is selected from the group consisting of BGTC, DOTAP, DOTMA, DMRIE, DOSPA, DOGS, DODAP, DODAB, CTAB, 1-DPPES, aminoglycoside lipid derivatives, and mixtures thereof.

4. The multimodular assembly according to claim 3, wherein said cationic lipid is mixed with a co-lipid selected from the group consisting of DOPE, DOPC, cholesterol, POPE, distearoyl-, palmitoyl- and myristoylphosphatidylethanolamine and their 1- to 3-fold N-methylated derivatives, phosphatidylglycerols, diacylglycerols, glycosyldiacylglycerols, cerebrosides, sphingolipids, asialogangliosides, and mixtures thereof.

5. The multimodular assembly according to claim 1, wherein said amphiphilic block co-polymer and said negatively charged macromolecule are present in a weight ratio ranging from 10 to 1200.

6. The multimodular assembly according to claim 1, wherein the targeting ligand is selected from the group consisting of monosaccharide or polysaccharide, RGD moiety, polylysine peptide, peptides, antibodies or fragments thereof, lectins, receptor ligands, growth factors, vitamins, and cytokines.

7. The multimodular assembly according to claim 1, wherein at least 50% of said hydrophilic blocks of said amphiphilic block co-polymer are end-conjugated with a targeting ligand.

8. The multimodular assembly according to claim 1, wherein said negatively charged macromolecule is selected from the group consisting of nucleic acid, peptide nucleic acid, protein, and antigen.

9. The multimodular assembly according to claim 1, wherein said multimodular assembly has a mean diameter ranging from 200 to 500 nm.

10. A vaccine composition comprising at least one multimodular assembly according to claim 1.

11. A gene therapy medicament comprising at least one multimodular assembly according to claim 1.

* * * * *